United States Patent [19]

Buckanin

[11] Patent Number: 4,705,840
[45] Date of Patent: Nov. 10, 1987

[54] CATALYSTS FOR THE CURING OF A WATER-CURABLE ISOCYANATE-FUNCTIONAL PREPOLYMER

[75] Inventor: Richard S. Buckanin, Woodbury, Minn.

[73] Assignee: Minnesota Mining and Manufacturing Company, St. Paul, Minn.

[21] Appl. No.: 784,344

[22] Filed: Oct. 4, 1985

[51] Int. Cl.$^4$ ............... C08G 18/08; B01J 31/00; C08L 15/00
[52] U.S. Cl. .................................... 528/53; 523/111; 502/167
[58] Field of Search .................. 502/167; 523/111; 528/53

[56] References Cited

U.S. PATENT DOCUMENTS

| 4,376,438 | 3/1983 | Straube et al. | 427/2 |
| 4,411,262 | 10/1983 | von Bonin et al. | 428/260 |
| 4,433,680 | 2/1984 | Yoon | 523/111 |
| 4,502,479 | 3/1985 | Garwood et al. | 128/90 |
| 4,574,793 | 3/1986 | Lee et al. | 528/53 |

OTHER PUBLICATIONS

H. Igarishi, et al., "On the Synthesis and Pharmacology of Basic-sec,tert-Alcohol and Derivatives", Yakugaku Zasshi, 93, 554, 563–564 (1973).

Primary Examiner—John Kight
Assistant Examiner—Dennis R. Daley
Attorney, Agent, or Firm—Donald M. Sell; James A. Smith; Dale E. Hulse

[57] ABSTRACT

New catalysts useful in the curing of a water-curable isocyanate-functional prepolymer are provided. The new catalyst is a new 2,2'-dimorpholinyldialkyl ether. The use of the improved catalyst provides prepolymer/catalyst premix compositions having equivalent or increased shelf stability and which, when water-cured, yield resins having superior early strengths. A method of curing an isocyanate-functional prepolymer and articles useful as orthopedic bandages are also provided.

17 Claims, No Drawings

CATALYSTS FOR THE CURING OF A WATER-CURABLE ISOCYANATE-FUNCTIONAL PREPOLYMER

FIELD OF THE INVENTION

This invention relates to new catalysts for the curing of a water-curable isocyanate-functional prepolymer. More particularly, this invention relates to new 2,2'-dimorpholinyldialkyl ethers and their use as catalysts in the curing of water-curable isocyanate-functional prepolymers.

BACKGROUND OF THE INVENTION

Orthopedic casts for use in the treatment of bone fractures or other conditions requiring immobilization of the body member are generally formed from a sheet of fabric or scrim material impregnated with a substance which hardens into a rigid structure after the sheet has been wrapped around the body member.

The orthopedic casts now most commonly used are comprised of a fiberglass scrim impregnated with a water-curable isocyanate-functional prepolymer. These casts when cured have a higher strength to weight ratio than plaster-of-paris, are impervious to water and provide excellent radiolucency. U.S. Pat. No. 4,411,262 (von Bonin) and U.S. Pat. No. 4,502,479 (Garwood) disclose water-curable isocyanate-functional prepolymers useful in orthopedic bandages.

The prepolymer typically includes a tertiary amine catalyst in an amount selected to optimize curing time. After the resin-impregnated scrim has been immersed in water, sufficient "working time", e.g., 3 to 5 minutes, should be provided in which the wrapping is accomplished and the cast is manually molded into shape. However, after the cast is shaped, the resin should harden rapidly, typically in 15-30 minutes and preferably less, into a rigid, high-strength, weight-bearing cast.

U.S. Pat. No. 4,376,438 (Straube et al.) discloses an orthopedic casting material wherein the tertiary amine catalyst is chemically linked to the polymer portion of the isocyanate functional prepolymer. No separate catalyst is required.

U.S. Pat. No. 4,502,479 (Garwood et al.) discloses the use of tertiary alkanolamines, e.g., dimethylethanolamine and dimethylaminodiethyl ether, as catalysts in the curing of a water-curable isocyanate functional prepolymer. At concentrations which do not adversely affect shelf stability, these simple catalysts do not cure as fast as desired by many experienced cast appliers.

U.S. Pat. No. 4,433,580 (Yoon) discloses the use of 2,2'-dimorpholinyldiethyl ether (DMDEE) as a catalyst in the cure of a water-curable isocyanate-functional prepolymer on an open-weave fibrous substrate to form an orthopedic bandage. The use of DMDEE is said to provide an orthopedic bandage having increased shelf-stability and acceptable set time.

Commercially available orthopedic bandages containing DMDEE typically contain about 2-3 percent by weight DMDEE (about 7.5-10 mole percent). These commercially available orthopedic bandages, while having acceptable shelf stability and set time, do not exhibit superior early strengths. Superior early strengths are particularly advantageous in the case of leg casts which must be weight bearing in a relatively short time after application to permit the patient to ambulate.

A journal article, H. Igarishi, et al., "On the Synthesis and Pharmacology of Basic-sec,tert-Alcohol and Derivatives", Yakugaku Zasshi, 93, 554, 563–564 (1973) discloses the preparation of a mixture of 1-methyl-2-N-morpholinoethyl 2'-morpholinoethyl ether dihydrochloride and 2-methyl-2-N-morpholinoethyl 2'-morpholinoethyl ether dihydrochloride and a mixture of di(1-methyl-2-N-morpholinoethyl) ether dihydrochloride and 2-methyl-2-N-morpholinoethyl 2'-methyl-2'-N-morpholinoethyl ether dihydrochloride and the pharmacological, e.g., antispasmodic and analgesic, activities of the respective mixtures.

SUMMARY OF THE INVENTION

This invention relates to a composition useful as a catalyst in the curing of a water-curable isocyanate-functional prepolymer resin comprising a substantially pure amino ether compound having the structural formula:

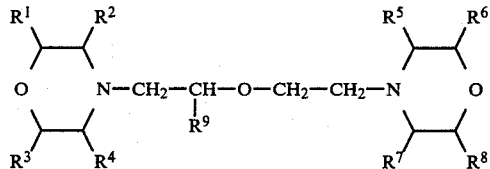

wherein:
each of $R^1$–$R^8$ are individually hydrogen or lower alkyl; and
$R^9$ is a methyl group or a phenyl group wherein the phenyl group may have one or more lower alkyl substituents.

As used herein, the term lower alkyl shall refer to alkyl groups having from about 1 to about 4 aliphatic carbon atoms.

The term "substantially pure" shall mean (a) a homogeneous physical phase having less than 50 percent by weight of an organic solvent for the amino ether compound preferably less than 10%, most preferably less than 1%, and/or (b) substantially isomerically pure, i.e., having less than 25 percent by weight of a position isomer of the amino ether compound, preferably less 10 percent.

This invention also relates to a method of catalyzing the curing of a water-curable isocyanate-functional prepolymer resin comprising forming a mixture of:
(a) water-curable isocyanate-functional prepolymer resin,
(b) water, and
(c) a catalytically effective amount of an amino ether compound having the above structural formula.

This invention also relates to a composition comprising an amino ether catalyst as described above and an isocyanate-functional prepolymer resin. These compositions are useful as adhesives, coatings and sealants and as the reinforcing resin for an orthopedic bandage. This invention also relates to an article comprised of a flexible sheet in contact with the above-described catalyst/resin composition. This invention also relates to a method of orthopedic casting using the above-described article.

It has been found that the use of the amino ether compounds having the above structural formula yield water-curable resin compositions having equivalent or better shelf stability and, when cured, yield resins having superior early strengths compared to the identical resins prepared with the same concentration of a catalyst of the prior art.

DETAILED DESCRIPTION OF THE INVENTION

The amino ether catalysts of this invention are 2,2'-dimorpholinyldialkyl ethers having the structural formula described above. The preparation of the amino ether compounds described above may be accomplished by the following reaction:

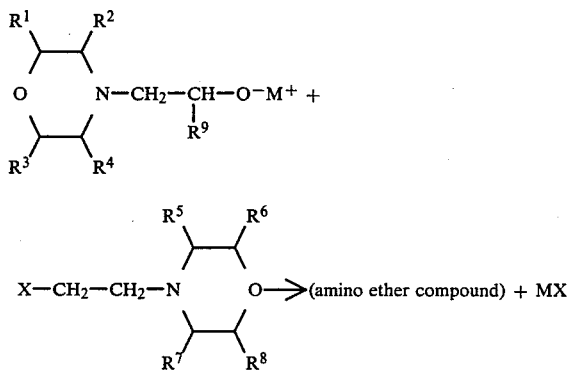

wherein $R^1$–$R^9$ are as previously described, M is an alkali or alkaline earth metal atom (e.g., Na or Ca), and X is a halogen atom (e.g., Cl). The above reaction is a variation of the type reaction known in the art as a Williamson ether synthesis. Such a reaction is conveniently conducted by dissolving an appropriate alcohol in an inert solvent (e.g., an aromatic hydrocarbon) and forming a corresponding alkoxide by the addition of an alkali metal (e.g., sodium) or sufficiently alkaline form thereof (e.g., hydride, oxide, etc.) and application of heat. The resulting alkoxide is then reacted with an appropriate alkyl halide, usually by dropwise addition of the alkyl halide to the alkoxide, to form the desired ether compound. The desired amino ether compounds can be isolated directly from the reaction mixture or the reaction mixture can be acidified to isolate the amino ether as an acid salt. It is believed that the salt must be neutralized at least partially to obtain a free amine functionality before the amino ether compound can be used as a catalyst as described hereinafter.

Representative compounds of this invention include:
4-[2-[1-methyl-2-(4-morpholinyl)ethoxy]-ethyl]-morpholine;
4-[2-[2-(4-morpholinyl)-1-methylethoxy]-ethyl]-2,6-diisopropylmorpholine;
4-[2-[-(4-(2,6-dibutylmorpholinyl))-1-methylethoxy]-ethyl]-2,6-dibutylmorpholine;
4-[2-[1-phenyl-2-(4-morpholinyl)ethoxy]-ethyl]-2-methylmorpholine;
4-[2-[1-methyl-2-(3-methyl-4-morpholinyl)-ethoxy]-ethyl]-morpholine;
4-[2-[1-methyl-2-(2-methyl-4-morpholinyl)-ethoxy]-ethyl]-morpholine;
4-[2-[2-(4-morpholinyl)propoxy]-ethyl]-3-methylmorpholine;
4-[2-[2-(4-morpholinyl)propoxy]-ethyl]-2-methylmorpholine;
4-[2-[2-(4-(3-methylmorpholinyl))-1-methylethoxy]-ethyl]-3-methylmorpholine;
4-[2-[2-(4-(3-methylmorpholinyl))-1-methylethoxy]-ethyl]-2-methylmorpholine;
4-[2-[2-(4-(2-methylmorpholinyl))-1-methylethoxy]-ethyl]-2-methylmorpholine.

The preferred compounds are those wherein $R^9$ is methyl or phenyl and $R^1$–$R^8$ are individually hydrogen or methyl, e.g., 4-[2-[-methyl-2-(4-morpholinyl)ethoxy]-ethyl]morpholine (hereinafter referred to as MEMPE).

The term "substantially pure" shall mean (a) a homogeneous physical phase having less than 50 percent by weight of an organic solvent for the amino ether compound preferably less than 10%, most preferably less than 1%, and/or (b) substantially isomerically pure, i.e., having less than 25 percent by weight of a position isomer of the amino ether compound, preferably less 10 percent. For example, the journal article by Igarishi discloses a method of preparing the dihydrochloride salts of amino ether compounds. That method of preparing this amino ether dihydrochloride involves the generation of corresponding free amines in a solution of an organic solvent for the amino ethers, e.g., diethyl ether. Accordingly, Igarishi does not disclose an amino ether compound which is substantially unsolvated.

Further, Igarishi purports to disclose the preparation of 1-methyl-2-N-morpholinylethyl 2'-N-morpholinylethyl ether dihydrochloride. Igarishi discloses that this compound is prepared by reacting the alkoxide of 2-morpholine-1- ethanol with 1-morpholine-2-chloropropane. However, 1-morpholine-2-chloropropane exists, in solution, in equilibrium with an ionic isomer as shown below.

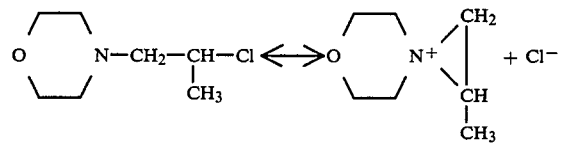

Because the alkoxide of 2-morpholine-1-ethanol can react with the ionic isomer at either of the isopropyl carbon atoms bonded to nitrogen, the reaction produces a solution mixture containing 2-methyl-2-N-morpholinylethyl 2'-morpholinylethyl as well as the desired 1-methyl-2-N-morpholinylethyl 2'-morpholinylethyl ether. Accordingly, the method disclosed by Igarishi cannot be used to prepare 1-methyl-2-N-morpholinylethyl 2'-morpholinylethyl ether substantially free from its position isomer without the use of laborious techniques to separate a mixture of the isomers. In contrast, the method of this invention employs reactants which do not yield a mixture of position isomers such that the method of this invention can be used to obtain amino ether compounds which are substantially isomerically pure.

The water-curable isocyanate-functional prepolymers useful in the present invention are known in the art. They are generally prepared by reacting a polyol with an excess of a polyisocyanate.

It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixtures of these isomers, 2,4'-diphenylmethane diisocyanate, 1,4'-diphenylmethane diisocyanate, mixtures of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde.

4,4'-Diphenylmethane diisocyanate is commonly known as "methylene diisocyanate" or "MDI". In its pure form MDI is commercially available as Isonate TM 125M from the Upjohn Co., and as Mondur TM M or Multrathane TM M from Mobay Chemical Corp. As used herein "isocyanate-functional derivatives of MDI" will be construed to include isocyanates actually prepared from MDI, and will also include isocyanates which have not actually been prepared from MDI but which have chemical structures capable of being prepared from MDI if desired. Isocyanate-functional derivatives of MDI which can be used in this invention include liquid mixtures of MDI and melting point modifiers (e.g., mixtures of MDI with polycarbodiimide adducts such as Isonate TM 143L, commercially available from the Upjohn Co., and Mondur TM CD, commercially available from Mobay Chemical Corp., and Rubinate TM M, commercially available from Rubicon Chemicals, Inc.) and blocked isocyanate compounds formed by reacting MDI or the above-described isocyanate-functional derivatives of MDI with blocking agents such as ketoximes, phenols, and the like. Such blocked isocyanate compounds will, for convenience, be regarded herein as isocyanate-functional derivatives will sometimes be referred to collectively herein as "MDI".

Typical polyols for use in the prepolymer system include polypropylene ether glycols and polyols (available from Union Carbide under the tradename Niax Polyol and from BASF Wyandotte under the tradename Pluracol TM ), polytetramethylene ether glycols (Polymeg TM from the Quaker Oats Co.), polycaprolactone polyols (Niax TM PCP series of polyols from Union Carbide), and polyester polyols (hydroxyl terminated polyesters obtained from esterification of dicarboxylic acids and diols such as the Rucoflex TM polyols available from Ruco division, Hooker Chemicals Co.).

The isocyanates and the polyols are reacted with one another under conventional polyurethane reaction conditions known to those skilled in the art. Preferably the NCO:OH ratio of the reactants is about 1.2:1 to 4.5:1, and most preferably is about 1.8:1 to 3.8:1. As the NCO:OH ratio is increased, the compositions of the invention tend to be less moisture sensitive and to have longer shelf life. Ordinarily, the prepolymer is prepared under a suitable atmosphere (e.g., nitrogen). It is convenient to add MDI to the reaction vessel first, followed by heating or addition of solvent if necessary to liquefy the MDI, followed by addition of polyols. Reactants which are in solid form are dissolved in a suitable solvent or melted prior to addition of the other reactants. The reaction mixture is maintained at about 50° C. to 70° C. until the desired isocyanate equivalent weight is obtained. The prepolymer can be separately stored for later use or any remaining ingredients of the compositions of the invention can be added to the reaction vessel.

As one example of an alternate method for preparation of prepolymers (e.g., prepolymers with a polyether backbone) used in this invention, one mole of a polytetramethylene oxide diol and containing about 2 mole of reactive hydroxyl groups is reacted with excess (i.e., more than 2 moles) phosgene in the presence of a low boiling alkylamine, (e.g., $(CH_3)_3N$) at about 0° C. in a closed reaction vessel to provide a di(carbamoyl chloride)-terminated polyether. This compound reacted with about 2.2 moles di(para-aminophenyl)methane in the presence of about 2.2 moles low boiling alkylamine to provide a di(amine)-terminated polyether polyurethane. This compound is reacted with excess phosgene in the presence of low boiling alkylamine at about 0° C. in a closed container to provide the desired prepolymer.

Regardless of the method of preparation of the prepolymer, the free isocyanate groups of the prepolymer can, if desired, be blocked to decrease moisture sensitivity, e.g., by reacting the prepolymer with a labile reagent that can be displaced during the subsequent curing of the prepolymer. Suitable blocking agents preferably do not require heat for deblocking, and include di(lower alkyl)malonates, ethyl acetoactate, isophorone, acetone, methyl ethyl ketone, and the like. Ordinarily, an excess of blocking agent is employed to assure that all free isocyanates groups of the prepolymer react with the blocking agent. It has been found that the compositions of the present invention are sufficiently stable that the use of a blocking agent is not ordinarily required. Elimination of the blocking agent can reduce cost and reduce the evolution of volatile substances during cure. Preferably, no blocking agents are employed in the composition of this invention.

The prepolymer should be stored until use in a container that is both moisture and oxygen impermeable to increase the shelf-life of the prepolymer. During storage the contact of the prepolymer with oxygen and moisture is accordingly minimized.

The prepolymer and amino ether catalyst are mixed using conventional mixing techniques. As with any storage of the prepolymer, the mixing should be done under anhydrous conditions, preferably in substantially inert atmosphere, e.g., nitrogen gas. The resulting prepolymer/catalyst mixture should also be stored under anhydrous conditions in a container substantially impermeable with respect to oxygen and moisture.

The prepolymer/catalyst compositions have properties which allow utility in a variety of applications including use as an adhesive, a coating, a sealant, a structural reinforcing resin, etc. When used as an adhesive, the composition is placed between an article and a substrate, in contact with both, and exposed to moisture sufficient to cure the resin. When used as a coating, the composition is deposited as a continuous layer on the surface of the article to be coated and exposed to moisture sufficient to cure the resin. When used as a sealant, the composition is deposited in the void to be sealed and exposed to moisture sufficient to cure the composition. When used as a structural reinforcing resin, the composition is coated onto and/or impregnated into an article comprised of a flexible sheet of fibrous or non-fibrous fabrics, papers, felts, foams and the like and exposed to moisture sufficient to cure the composition. The compositions are particularly useful when applied to porous flexible sheets which can then be exposed to moisture to form hardened orthopedic bandages.

Orthopedic Bandages and Other Sheet Material Articles

One of the most advantageous uses of the prepolymer/catalyst composition of this invention is the use of the composition as a coating for a flexible sheet, which coating hardens on exposure to moisture.

An especially preferred resin for use in the casting material of the invention uses an isocyanate known as Isonate TM 143L available from the Upjohn Company (a mixture containing about 73% of MDI) and a polypropylene oxide polyol available from Union Carbide as Niax TM PPG 725. To prolong the shelf-life of the material, it is preferred to include about 0.02-0.1 percent by weight of benzoyl chloride or other suitable stabilizer.

The reactivity of an isocyanate-functional prepolymer once it is exposed to water as a curing agent is controlled by the amino ether catalysts described above. An effective amount of the amino ether compound is the amount necessary to achieve the desired degree of reactivity.

The reactivity must not be so great that: (1) a hard film quickly forms on the resin surface preventing further penetration of the water into the bulk of the resin; or (2) the cast becomes rigid before the application and shaping is complete. The precise amount of amino ether catalyst will depend upon the nature of the isocyanate-functional prepolymer, but will generally range from about 0.1% to about 5% by weight of the isocyanate-functional prepolymer, preferably from about 0.1 to about 3%, most preferably from about 1.0 to about 2%.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, in order to have reactivity, workability, shelf-life and ultimate strength, an adequate concentration of isocyanate groups is necessary. Although foaming is less at low resin contents, adequate resin content is required for desirable cast characteristics such as strength and resistance to peeling. It has been found that the most satisfactory method of minimizing foaming is to add a foam suppressor such as silicone Antifoam A (Dow Corning), DB-100 silicone fluid (Dow Corning), or silicone surfactants L550 or L5303 (Union Carbide) to the resin. It is preferred to use a silicone liquid such as Dow Corning DB-100 at a concentration of about 0.1 to 1.0 percent by weight.

The sheet material articles of this invention, useful as orthopedic bandages, are preferably prepared by mixing an isocyanate-functional prepolymer with an ether catalyst as described above and coating the resulting premix onto a flexible sheet, e.g., a fabric. The sheet material articles of this invention may also be used outside the field of orthopedic bandages, i.e., wherever a fabric reinforced sheet of water-cured resin is useful, e.g., in repairing a variety of structures such as repairing a breach in a cable jacket or conduit.

In the preferred embodiments relating to sheet materials, a porous, flexible sheet material will be impregnated with the composition. A preferred example of a porous, flexible sheet material which may be impregnated with the compositions of this invention is disclosed in U.S. Pat. No. 4,502,479, incorporated herein by reference thereto. The fabric therein is stated to impart high structural strength to an orthopedic bandage prepared therefrom.

A particularly preferred fabric for use in the orthopedic bandages of this invention is disclosed in U.S. application Ser. No. 668,881, filed Nov. 6, 1984, the disclosure of which is incorporated herein by reference thereto. This fabric is used in the orthopedic bandage available from 3M as Scotchcast TM 2 Casting Tape. The fabric is a fiberglass fabric comprised of extensible knit fiberglass which exhibits an extensibility of at least about 20% in the length direction and has been set to reduce fraying.

The fabric used in the casting material is generally formed in rolls of various widths, generally from one inch to six inches wide. The fabric is impregnated with the curable resin material in an amount, in terms of volume, of from one to three times the volume of the material forming the fabric, and in the preferred embodiment employing a fiberglass fabric of from 40% to 50% by weight of the impregnated casting material. The term "impregnate" is used to describe the condition in which the polymer is thoroughly intermingled with and in surrounding relation to the threads of fibers of the fabric and does not necessarily indicate that the resin is to any extent absorbed by the fibers themselves. Generally, the resin solution will flow into the capillary spaces between contiguous filaments of the fabric and will become rigidly bonded to the fabric upon curing.

The amount of resinous component applied to the fabric for an orthopedic bandage must be sufficient for the formation of a strong interlayer laminate bond but not so much as to occlude the porosity and unnecessarily thicken the resin film which should be thin for rapid and complete hardening. Excessive resinous component may also cause the casting tape to be messy to handle because of stickiness or dripping and transfer of resin.

The resin coated tape may be in the form of a roll wound up on a plastic core sealed within a moisture and oxygen impermeable container. For use, the container is opened and the roll is fully immersed in tap water for about 5 to 30 seconds. This is sufficient time for water to seep into the porous material and displace air. As long as the resin content is not too high to cause the openings in the fabric to be filled with resin, more than enough water is absorbed by the roll in this manner. The roll may be squeezed underwater to replace entrapped air with water. When the roll is unwound during wrapping of the cast, the excess moisture coats freshly exposed resin surfaces insuring thorough wetting and rapid hardening of the cast. An alternate method comprises wrapping the cast without dipping and then allowing atmospheric moisture or water provided by spraying or by application of a wet towel to cure the prepolymer.

Prior to applying the orthopedic cast, protective padding is positioned about the limb or body member of the patient. The padding may take the form of a tubular stockinet or some other convenient form such as for example an elongated strip or bandage which may be wrapped about the body member.

With the padding in a proper position, the moistened orthopedic cast material is wrapped about the body member and over the protective padding in a manner similar to the application of an elastic-type bandage. The cast is shaped in a manner similar to the shaping of a plaster-of-paris cast.

Eight or fewer layers of the cast material should be sufficient to form a cast having weight-bearing strength within 30 minutes, i.e., a cylindrical laminate having eight or fewer layers should support 20 pounds of pressure per inch of cylinder length, and significant strength should develop within $7\frac{1}{2}$ minutes. The tests to determine these strengths are discussed more fully below.

Adhesives, Coatings and Sealants

The compositions of this invention comprised of the isocyanate-functional prepolymer resin and the amino ether compounds of this invention will be useful in a variety of applications wherein isocyanate-functional prepolymers have been used previously, i.e., as sealants (e.g. caulks), coatings, adhesives, etc., as well as a reinforcing resin for an orthopedic bandage.

In addition to the polyols described above as useful in preparing an isocyanate-functional prepolymer, polyols having primary hydroxyl groups as disclosed in U.S. Pat. No. 4,511,626, the entire disclosure of which is incorporated herein by reference thereto, are especially useful.

As used herein, a "primary hydroxyl group" is a monovalent radical having a hydroxyl radical bonded to a methylene radical. Similarly, "secondary hydroxyl group" will be used herein to refer to a monovalent radical having a hydroxyl radical bonded to a methylidyne radical. As used herein, a "primary polyol" is a polyol containing two or more primary hydroxyl groups. Similarly, "secondary polyol" will be used herein to refer to polyols containing two or more secondary hydroxyl groups. Polyols containing both primary hydroxyl groups and secondary hydroxyl groups will be regarded herein as primary polyols if the primary hydroxyl groups thereof are reactive with MDI.

Suitable primary polyols have a backbone containing, for example, aliphatic, olefinic, ether, ester, thioether, urethane or urea linkages. Primary polyols containing ether linkages (e.g., those having a polyether backbone) are preferred. The primary polyols have a number average molecular weight between about 90 and 8000, most preferably between about 200 and 3000. The primary polyols preferably have 2 to 4 primary hydroxyl groups per molecule. Expressed in terms of hydroxyl equivalent weights, the primary polyols preferably have a hydroxyl equivalent weight between about 45 and 2500, most preferably between about 100 and 1500. "Hydroxyl number", as used herein, refers to the number of milligrams of KOH having the same hydroxyl content as one gram of the polyol. "Hydroxyl equivalent", as used herein, refers to the quotient obtained by dividing the number average molecular weight of the polyol by the number of hydroxyl groups therein. "NCO equivalent", as used herein refers to the quotient obtained by dividing the number average molecular weight of an isocyanate by the number of reactive isocyanate groups therein.

Suitable primary polyols for use in this invention include polytetramethylene oxide glycols, ethylene oxide-terminated polypropylene glycols, polyethylene glycols, hydroxyl-terminated polybutadienes, aliphatic glycols, polyester polyols (e.g., polyacrylate polyols or polycaprolactone polyols), fatty alcohols, and triglycerides (e.g., castor oil). Mixtures of primary polyols can be used if desired.

Suitable commercially available primary polyols include Pluracol TM TPE 4542 ethylene oxide-terminated polypropylene glycol, commercially available from BASF/Wyandotte Corp., Voranol TM E series polyethylene glycols, commercially available from Dow Chemical Co., QO Polymeg TM 650, 1000, or 2000 series polytetramethylene oxide glycols, commercially available from Quaker Oats, Co., Teracol TM 2000 polytetramethyleneoxide glycol, commercially available from E. I. duPont de Nemours & Co., Inc., Niax TM series PCP TM, and Capped Polyols TM, as well as Polymer Polyols TM and "Mixed Oxide Polyols" containing primary hydroxyl groups, commercially available from Union Carbide Corp., Poly-G TM 53-, 55-, 56-, 85-, and 86- series ethylene oxide terminated polypropylene glycols, commercially available from Olin Chemicals, Poly bd TM hydroxyl-terminated polybutadienes, commercially available from ARCO-Chemical Co., and Multron TM and Multrathane TM polyester polyols, commercially available from Mobay Chemical Co.

A preferred subclass of primary polyols for use in this invention are polytetramethylene oxide glycols, particularly those having a number average molecular weight from about 650 to 2000, preferably from about 1000 to 2000. Another preferred subclass of primary polyols for use in this invention are ethylene oxide-terminated polypropylene glycols, particularly those having a number average molecular weight from about 500 to 3000, preferably from about 1000 to 2000. A third preferred subclass of primary polyols for use in this invention are polycaprolactone polyols, particularly those having a number average molecular weight from about 300 to 3000, preferably about 800 to 2000.

For optimum shelf life in the compositions of this invention, it is preferred that the primary polyol(s) have a pH between about 5.5 and 7. Most preferably, the pH of the primary polyols is between about 6 and 6.5.

If desired, the prepolymers used in this invention can be derived from reaction mixtures containing MDI and primary polyols together with additional reactants such as aromatic isocyanates (e.g., 2,4-toluene diisocyanate, hereafter referred to as "TDI"), secondary polyols, or other additional reactants which do not materially detract from the functioning of the prepolymer in the compositions of this invention. For example, it is frequently desirable to employ secondary polyols in the reaction mixture from which the prepolymers are prepared, in order to adjust the handling properties, physical properties, or cure characteristics of the compositions of the invention. Preferably, the polyols in the prepolymer reaction mixture are about 25 to 100 weight percent primary polyols and 0 to 75 weight percent secondary polyols, and most preferably about 40 to 80 weight percent primary polyols and 20 to 60 weight percent secondary polyols. Suitable secondary polyols include polypropylene ether diols and higher polyalkylene ether diols (e.g., polybutylene ether diols), polyalkylene ether triols (e.g., those prepared by condensing a lower alkylene oxide such as ethylene oxide or propylene oxide with an alkylene triol such as glycerine, trimethylopropane, or the like), and polyols with tetra- or higher functionality such as pentaerythritol, sorbitol, and the like.

Preferred secondary polyols include propylene oxide-terminated ethylene oxide glycols and polypropylene glycols. Suitable commercially available secondary polyols which can be incorporated into prepolymers for use in this invention include Niax TM series "PPG", "LG", "LHT", and "Special Purpose Polyols" containing secondary hydroxyl groups, commercially available from Union Carbide Corp., Pluracol TM series polyols containing secondary hydroxyl groups, commercially available from BASF/Wyandotte Corp., Voranol P TM series polypropylene glycols, commercially available from Dow Chemical Co., and Poly-G TM 20- and 30- series polypropylene glycols, commercially available from Olin Chemicals.

As used herein, an "effective amount" of an ingredient is an amount sufficient to provide desired physical properties (e.g., cure rate or tensile strength) in the compositions of the invention. An effective amount of amino ether compound preferably is about 0.002 to 2 weight percent, and most preferably about 0.05 to 0.5 weight percent based upon the weight of prepolymer.

The prepolymer and amino ether are mixed using conventional mixing techniques. Preferably the amino ether is dissolved in a suitable solvent (e.g., toluene) and added to the prepolymer. The resulting mixture should be stored in a sealed container until the time of use.

The mixture of prepolymer and amino ether can contain other ingredients or adjuvants if desired. It is also preferred to include an effective amount of other adjuvants such as extender and/or reinforcing fillers (e.g., carbon black, metal oxides such as zinc oxide, and minerals such as talc, clays, silica, silicates, and the like) in the compositions of the invention. Carbon black is a particularly preferred filler for use where resistance to degradation caused by ultraviolet light exposure is desired, e.g., for use in windshield sealants. An effective amount of filler preferably is between about 0 and 80 weight percent based upon the weight of prepolymer and most preferably between about 20 and 60 weight percent.

Solvents such as toluene, xylene, methyl ethyl ketone, acetone, ethyl acetate, Cellosolve ™ Acetate (commercially available from Union Carbide Corp.), and other suitable materials free of isocyanate-reactive moieties can be employed in these compositions of this invention. Toluene is a preferred solvent. An effective amount of solvent preferably is between about 0 and 80 weight percent based upon the weight of prepolymer.

Plasticizers such as partially hydrogenated terphenyls (e.g., "HB-40", commercially available from Monsanto Corp.), dioctyl phthalate, dibutyl phthalate, diisodecyl phthalate, or tricresyl phosphate can also be employed in these compositions of this invention. Partially hydrogenated terphenyls are a preferred plasticizer. An effective amount of plasticizer preferably is between about 0 and 25 weight percent based upon the weight of prepolymer.

In addition, the compositions of the invention can contain antioxidants, pigments, UV absorbers, adhesion promoters, drying agents (e.g., molecular sieves such as sodium aluminum silicate or dessicants such as zeolite, silica gel, barium oxide, or calcium oxide), and the like.

For use in glass sealant compositions, it is desirable to employ an effective amount of a silane-containing primer, either as an ingredient of the sealant composition, or as a separate layer placed between the surface of the glass to be sealed and the layer of sealant, or as both an ingredient of the sealant composition and as a separate layer. Suitable silane-containing primers are described in U.S. Pat. Nos. 3,627,722 and 3,707,521. If silane-containing primer is incorporated into a sealant composition of this invention, an effective amount of silane-containing primer preferably is between about 2.5 and 10 weight percent, based upon the weight of prepolymer. If silane-containing primer is employed as a separate primer coating, then an effective amount of such silane-containing primer in the primer coating will be an amount which gives the desirous degree of bonding performance given the mode of application of the primer layer and the sealant composition to the surfaces which are to be bonded.

A particularly preferred prepolymer/catalyst composition for use as an adhesive coating or sealant will also contain an effective amount of a terpene-phenolic resin in addition to the silane described above. The compositions have excellent adhesion to unprimed metal, glass and concrete even when exposed to moisture or ultraviolet radiation. These compositions are more particularly described in U.S. application Ser. No. 697,831, filed Feb. 4, 1985, now U.S. Pat. No. 4,539,345.

The compositions of the invention can be put up in packages in accordance with techniques known to those skilled in the art. Suitable packages include, for example, caulking tubes (made, for example, of paper, metal, or plastic), screw-capped squeezable tubes, cans, drums, and the like.

The compositions of the invention are cured by exposure to water, e.g., water vapor or moisture. Ordinary ambient humidity is usually adequate to promote cure. Heat or high humidity will accelerate cure, and low temperatures (e.g., 5° C. or less) or low humidity (e.g., 15% R.H. or less) will retard cure. Bonds to damp substrates (e.g., wood) typically cure faster than bonds to dry substrates (e.g., glass).

The compositions of the invention can be employed in any application where a high-performance, rapidly-curing adhesive, coating, or sealant is desired. One such use includes the bonding of glass (e.g., windshields and backlights) to vehicles, either at the time of original manufacture or at the time of glass replacement, in vehicles such as automobiles, trucks, aircraft, trains, and the like. When so used, the compositions of the invention provide rapid drive-away times following glass installation. Other uses include building construction (e.g., as a structural adhesive, panel adhesive, moisture barrier, or glazing sealant), assembly line manufacturing (e.g., for assembly of parts by adhesive bonding), and coatings (e.g., deck coatings or roof membranes). The compositions of the invention can be applied to a variety of articles and substrates, such as articles or substrates of glass, metal, plastic, wood, leather, masonry, textiles, and the like.

EXAMPLES

EXAMPLES 1-5

Preparation of Catalysts for Orthopedic Bandages

EXAMPLE 1

4-[2-[1-methyl-2-(4-morpholinyl)ethoxy]-ethyl]-morpholine

An amount, 871.2 grams, of morpholine (10 moles) and 580.8 grams of propylene oxide (10 moles) were mixed in a 2 liter flask and set aside for seven days at room temperature. At the end of this time, the solution was distilled under vacuum to give 1396.0 grams (96.1%) of N-(2-hydroxypropyl)-morpholine as a colorless oil, bp 63°–65° C. at 0.25 mm of Hg. Gas chromatographic analysis of the product showed the presence of only one compound which indicated no position isomer was formed. The identity of the product was confirmed by elemental analysis, calc. 57.9 C, 10.4 H, 9.65 N; found 57.5 C, 10.3 H, 9.5 N.

One liter of dry toluene was placed in a five liter three necked round bottom flask equipped with a condensor, nitrogen inlet, overhead stirring motor and an additional funnel. The system was flushed with dry nitrogen for five minutes. 115.0 grams of clean sodium metal (5 moles) was cut into pieces and added to the toluene. The toluene was heated to reflux whereupon the sodium melted. Moderate agitation was required to form small droplets of the metal, which facilitated reaction with the alcohol. 726.0 grams of N-(2-hydroxypropyl)-morpholine (5 moles) prepared above was added dropwise to the flask by means of the addition funnel. A moderate exothermic reaction ensued. After addition of the alcohol was completed, the reaction was stirred at reflux overnight.

A solution of N-chloroethyl morpholine in toluene was prepared in the following manner. 930.4 grams of N-chloroethyl morpholine hydrochloride (5 moles) available commercially from Aldrich Chemical Co. was dissolved in 500 milliliters water. A solution of 300.0 grams of sodium hydroxide in 300 milliliters water was slowly added to the hydrochloride solution keeping the temperature below 35° C. during addition. After all the hydroxide solution had been added, the reaction was allowed to stir at room temperature for five minutes and then transferred to a separatory funnel. The upper layer was separated and the bottom layer was washed with 500 milliliters toluene. The combined organic layers were dried with anhydrous potassium carbonate, filtered and added in a slow stream to the refluxing alkoxide solution prepared above. After addition the reaction was refluxed overnight.

The reaction was cooled to room temperature and 250 milliliters of water were added. The solution was filtered and toluene was removed by distillation under reduced pressure. The residue was distilled under hi-vacuum to yield 875 grams (67.7%) of catalyst as a pale yellow oil, bp 118°–119° C. at 0.3 mm of Hg. The presence of one compound was indicated by GC analysis and the structure confirmed as that of the title compound by proton NMR and carbon-13 NMR and elemental analysis, calc. 60.4 C, 10.1 H, 10.9 N; found 60.0 C, 9.8 H, 10.8 N.

An amount, 2500.0 grams, of Isonate 143L (modified diphenylmethane diisocyanate) was added to a five liter three-necked round bottom flask equipped with a thermometer, stirrer and nitrogen inlet. To this was added 80.2 grams of the above catalyst (corresponding to an amount equivalent to 5 moles of tertiary amine per 100 moles of the free NCO groups, i.e., 5 mole %), 4.2 grams of benzoyl chloride and 10.0 grams of Dow-corning DB-100. This was followed by the addition of 221.0 grams of a 10% solution of BHT (2,6-di-tert-butyl-4-methylphenol) in PPG-725 then by 1781.8 grams of PPG-725. The equivalent ratio of NCO to OH was 3.5:1. The addition of the polyol was made through a dropping funnel over a period of thirty minutes. After addition the polymerization reaction was carried out at 50°–60° C. for one hour.

The prepolymer was machine coated in an atmosphere substantially free of moisture on a three inch wide strip of fiberglass fabric to give the tape containing 40% by weight of the resin. It was then cut in 4 yard lengths and packaged in foil pouches for storage and later use and evaluation.

In addition to the strength testing described below, rolled samples of the examples were stored in sealed envelopes similar to those used to store similar commercial items. These sealed samples were subjected to accelerated aging tests, i.e., held at elevated temperatures and then unwound in such a manner that the force needed to unwind the rolls could be measured. The samples of this invention exhibited commercially acceptable aging results which were comparable to, and often superior to, the comparative samples.

EXAMPLE 2

4-[2-[2-(4-(2,6-dimethylmorpholinyl))-1-methylethoxy]-ethyl]-morpholine

The compound 2,6-dimethyl-N-(2-hydroxypropyl) morpholine was prepared by the method of Example 1 from 100.56 grams 2,6-dimethylmorpholine (0.87 moles) and 50.53 grams of propylene oxide (0.87 moles). Distillation of the reaction mixture gave 116.1 grams (76.8%) of the alcohol as a pale yellow oil, bp 70°–72° C. at 0.25 mm of Hg. The following elemental analysis was obtained: calc. 62.4 C, 11.1 H, 8.1 N; found 62.0 C, 10.8 H, 8.0 N.

An amount, 398.5 grams, of 2,6-dimethyl-N-(2-hydroxypropyl) morpholine (2.3 moles) was condensed with the free chloroamine obtained from 390.5 grams N-chloroethyl morpholine hydrochloride (2.3 moles) as described above to give 325.4 grams (55.7%) of the catalyst as a pale yellow oil, bp 122°–124° C. at 0.3 mm of Hg. The structure was confirmed by elemental analysis, calc. 62.9 C, 10.6 H, 9.8 N; found 62.2 C, 10.4 H, 9.8 N.

This catalyst was formulated, coated and tested as described in Example 1.

EXAMPLE 3

4-[2-[2-(4-morpholinyl)-1-methylethoxy]-ethyl]-2,6-dimethylmorpholine

An amount, 437.9 grams, of N-(2-hydroxypropyl)-morpholine (3 moles) was condensed with the free chloroamine obtained from 642.0 grams N-chloroethyl-2,6-dimethylmorpholine hydrochloride (3.0 moles) as described above to give 554.8 grams (64.7%) of the catalyst, bp 122°–124° C. at 0.3 mm of Hg. The structure was confirmed as that of the title compound by elemental analysis, calc. 62.9 C, 10.6 H, 9.8 N; found 62.8 C, 10.8 H, 9.8.

This catalyst was formulated, coated and tested as described in Example 1.

EXAMPLE 4

4-[2-[2-(4-(2,6-dimethylmorpholinyl))-1-methylethoxy]-ethyl]-2,6-dimethylmorpholine An amount, 389.3 grams, of 2,6-dimethyl-N-(2-hydroxypropyl) morpholine (2.25 moles) was condensed with the free chloroamine obtained from 481.5 grams N-chloroethyl-2,6-dimethylmorpholine hydrochloride (2.25 moles) as described above to give 415.9 grams (58.8%) of the catalyst, bp 127°–129° C. at 0.3 mm of Hg. The structure was confirmed as that of the title compound by elemental analysis, calc. 64.9 C, 10.9 H, 8.9 N; found 64.4 C, 10.6 H, 8.9 N.

This catalyst was formulated, coated and tested as described in Example 1.

EXAMPLE 5

4-[2-[1-phenyl-2-(4-morpholinyl)ethoxy]-ethyl]-morpholine

N-(2-hydroxy-2-phenethyl) morpholine was prepared by the method Example 1 from 213.9 grams morpholine (2.46 moles) 304.1 grams of styrene oxide (2.46 moles). Recrystallization of the reaction mixture from 2500 ml of ethyl acetate/hexane (1:4) gave the alcohol as a colorless solid, mp 78°–80° C.

An amount, 828.0 grams, of N-(2-hydroxy-2-phenethyl) morpholine (4 moles) was condensed with the free chloroamine obtained from 744.3 grams N-chloroethyl-morpholine hydrochloride (4 moles) as described above to give 626.4 grams (48.9%) of the catalyst, bp 180° C. at 2 mm of Hg. The structure was confirmed as that of the title compound by elemental analysis, calc. 67.5 C, 8.8 H, 8.7 N; found 67.2 C, 9.0 H, 8.7 N.

This catalyst was formulated, coated and tested as described in Example 1.

Ring Strength Test Procedure

The following test is used to determine the strength of a 5.8 cm (2-inch) diameter cylindrical ring of a cured orthopedic bandage in accordance with this invention when compressed at specified test times after exposure to water.

A 7.6 cm (3-inch) wide and 101.6 cm (40-inch) long sample of fiberglass scrim impregnated with isocyanate functional prepolymer resin and catalyst prepared as described in the examples below is used as a test specimen. The test environment was maintained at 24° C. ±1.5° C. and 55 percent ±5 percent relative humidity. The tape was maintained in a substantially water-free environment from its manufacture until testing.

To begin testing, a 5.8 cm (2 inch) diameter mandrel was covered with a length of 5.8 cm (2 inch) diameter stockinette. A roll of the tape was immersed in an 27° C. ±0.5° C. water bath. After 30 seconds, the tape was removed from the water by the ends of the core and gently shaken to minimize dripping. The loose end of the tape was attached to the stockinette and the tape was manually unwound and cut to a length of approximately 100 cm (40 inches). A 1.65 kg (¾ lb.) weight was attached to the cut end of the tape such that the tape and weight dangled freely below the mandrel. Six layers of tape were then uniformly wound about the mandrel, the excess tape was cut off, and the end of the tape was generally smoothed with very light pressure. No single layer of tape extended beyond any of the other layers by more than 0.47 cm (3/16 of an inch). The ring was completely wound by 30 seconds after removal of the water bath.

The ring and stockinette were removed from the mandrel just prior to the time of compression testing. The ring specimen was mounted in a specially designed compression test fixture. The text fixture was comprised of two bars, 1.90 cm (¾ inches) in width 1.27 cm (½ inch) thick and 15.2 cm (6 inches) long, fixed 3.81 cm (1½ inches) apart. A penetrating bar, of same dimension as the fixed bars, was placed in the jaws of an Instron Model 1122. The ring was deposited on the two fixed bars and the fixture was placed in the Instron such that the seam of the wound roll was ⅛" to ¼" beyond where the penetrating bar contacted the test specimen from above. The crosshead setting of the Instron was set at 2 inches per minute and the full scale load was set to accommodate the expected compression strength such that the expected force to crush approximately 50–60 percent of the full scale load. The results of the compression testing when done at different times for different samples are shown in the tables below. The 7½ min. strength test has been found to correlate closely with the clinical set time of the casting material.

A series of orthopedic bandages of this invention were prepared and tested as described above. Examples of this envention are indicated by a numeral and comparative examples by a large case letter.

STRENGTH TESTING OF EXAMPLES 1 AND 5 AND COMPARATIVE EXAMPLES A–D

Two mono-substituted amino ether compounds of of this invention, i.e., those of Examples 1 and 5 wherein $R^1$–$R^8$ are hydrogen and $R^9$ methyl or phenyl, are shown below in Table I. The use of the compound DMDEE as the catalyst is shown in Comparative Example A and the use of alkyl groups other than methyl as $R^9$ are shown in Comparative Examples B–D.

TABLE I

Strength of Orthopedic Bandages Prepared With Mono-substituted Amino Ether Compounds $$O\diagup\diagdown N-CH_2-CH(R^9)-O-CH_2-CH_2-N\diagup\diagdown O$$

| | | Catalyst Level | | | |
| | | 5 mole % | | 10 mole % | |
| | | Strength at | | | |
| Example | $R^9$ | 7½ min | 30 min | 7½ min | 30 min |
| A | —H | 3.9 | 18.9 | 8.9 | 22.3 |
| 1 | —CH$_3$ | 8.1 | 21.3 | 11.4 | 24.3 |
| B | —C$_2$H$_5$ | 5.1 | 18.0 | 9.2 | 20.1 |
| C | n-C$_4$H$_9$ | 4.2 | 18.0 | — | — |
| D | n-C$_8$H$_{17}$ | 4.3 | 17.3 | 7.9 | 18.1 |
| 5 | phenyl | 7.0 | 24.5 | 10.0 | 24.8 |

The results shown in Table I illustrate that the substitution of an amino ether compound at $R^9$ with methyl or phenyl yields a catalyst which in turn yield casts having improved early strengths as shown by the strengths at 7½ min.

By comparing the strength at 7½ min. using 5 mole % of the catalyst of Example 1 with the strength at 7½ min. using 10 mole % of the prior art catalyst of Example A, it can be seen that at least one embodiment of this invention allows for the use of approximately one-half the amount of catalyst to obtain comparable set time.

STRENGTH TESTING OF EXAMPLES 2–4 AND COMPARATIVE EXAMPLES E–J

Another series of orthopedic bandages was prepared and tested as described above. The amino ether compounds of this invention, shown in Examples 2–4, were substituted in the $R^9$ position with methyl and in the $R^1$, $R^3$, $R^6$ and/or $R^8$ positions with methyl. The comparable amino ether compounds wherein $R^9$ is hydrogen or ethyl are shown for comparison in Comparative Examples E–J.

TABLE II

Strength of Orthopedic Bandages Prepared With Multiply-substituted Amino Ether Compounds $$R^1,R^3\diagup\diagdown O\diagup\diagdown N-CH_2-CH(R^9)-O-CH_2-CH_2-N\diagup\diagdown O\diagup\diagdown R^6,R^8$$

| | | | | | | Catalyst Level | | | |
| | | | | | | 5 mole % | | 10 mol % | |
| | | | | | | Strength at | | | |
| Example | $R^9$ | $R^1$ | $R^3$ | $R^6$ | $R^8$ | 7½ min | 30 min | 7½ min | 30 min |
| E | H | Me | Me | H | H | 4.2 | 17.8 | 8.3 | 21.2 |

TABLE II-continued
Strength of Orthopedic Bandages Prepared
With Multiply-substituted Amino Ether Compounds $$\begin{array}{c} R^1 \\ \diagdown \\ O \\ \diagup \\ R^3 \end{array} N-CH_2-CH-O-CH_2-CH_2-N \begin{array}{c} R^6 \\ \diagup \\ O \\ \diagdown \\ R^8 \end{array}$$
$$\quad\quad\quad\quad\quad\quad\quad |$$
$$\quad\quad\quad\quad\quad\quad R^9$$

| | | | | | Catalyst Level | | | |
|---|---|---|---|---|---|---|---|---|
| | | | | | 5 mole % | | 10 mol % | |
| | | | | | Strength at | | | |
| Example | $R^9$ | $R^1$ | $R^3$ | $R^6$ | $R^8$ | 7½ min | 30 min | 7½ min | 30 min |
| 2 | Me | Me | Me | H | H | 6.4 | 20.9 | 10.0 | 24.1 |
| F | Et | Me | Me | H | H | 4.9 | 19.6 | 9.0 | 21.8 |
| G | H | H | H | Me | Me | 4.2 | 17.8 | 8.3 | 21.2 |
| 3 | Me | H | H | Me | Me | 5.9 | 19.4 | 9.9 | 22.0 |
| H | Et | H | H | Me | Me | 3.5 | 18.1 | 7.6 | 19.8 |
| I | H | Me | Me | Me | Me | 1.9 | 16.1 | 7.0 | 18.6 |
| 4 | Me | Me | Me | Me | Me | 6.2 | 20.8 | 10.5 | 24.2 |
| J | Et | Me | Me | Me | Me | 3.4 | 16.9 | 8.5 | 19.7 |

("Me" is —CH₃ and "Et" is —C₂H₅)

The results shown in Table II, above, illustrate that the substitution of the amino ether compounds of this invention with methyl groups on the morpholinyl rings does not defeat the relative general superiority of those compounds over the corresponding compounds having hydrogen or ethyl at the $R^9$ position.

EXAMPLE 6 AND COMPARATIVE EXAMPLES K, L AND M

A contemporaneously prepared and tested series of Examples prepared and tested as in the preceding Examples gave the results shown in Table III.

TABLE III
Strength of Contemporaneously Prepared and Tested Orthopedic Bandages $$\begin{array}{c} \diagup \diagdown \\ O \\ \diagdown \diagup \end{array} N-CH-CH-O-CH-CH_2-N \begin{array}{c} \diagup \diagdown \\ O \\ \diagdown \diagup \end{array}$$
$$\quad\quad\quad\quad | \quad\quad | \quad\quad\quad |$$
$$\quad\quad\quad\quad R^{10} \quad R^9 \quad\quad R^{11}$$

| | | | | Catalyst Level | | | |
|---|---|---|---|---|---|---|---|
| | | | | 5 mole % | | 10 mole % | |
| | | | | Strength at | | | |
| Example | $R^9$ | $R^{10}$ | $R^{11}$ | 7½ min | 30 min | 7½ min | 30 min |
| K | H | H | H | 3.8 | 16.8 | 7.4 | 19.3 |
| 6 | —CH₃ | H | H | 8.5 | 18.7 | — | — |
| L | H | —CH₃ | H | 4.7 | 17.0 | 10.0 | 20.6 |
| M | CH₃ | —H | CH₃ | 2.3 | 16.7 | 6.8 | 17.6 |

The results in Table III illustrate that an alpha-methyl substituted amino ether compound of this invention yields casts which possess early strength superior to casts prepared with similar compounds wherein: (1) $R^9$ is hydrogen and $R^{10}$ is hydrogen, (2) $R^9$ is hydrogen and $R^{10}$ is methyl and (3) $R^9$ and $R^{11}$ are methyl.

ADHESIVE FORMULATIONS EXAMPLES 7 AND 8 AND COMPARATIVE EXAMPLES N, P AND Q

An isocyanate-functional prepolymer was prepared by combining 315 parts 4,4,'-diphenylmethane diisocyanate and 400 parts "LHT 28" polyol (a 6000 M.W. triol containing secondary hydroxyl groups, commercially available from Union Carbide Corporation) in a closed reaction vessel equipped with a stirrer and a nitrogen atmosphere. The resulting mixture was heated to 60° C. to melt the diisocyanate. Next, 1000 parts Polymeg TM 2000 polyol (a 2000 M.W. diol having primary hydroxyl groups, commercially available from Quaker Oats Co.) was heated to 60° C. and added to the reaction vessel, followed by addition of 66 parts "HB-40" plasticizer (a partially hydrogenated terphenyl, commercially available from Monsanto Corp.). After addition of all ingredients, the reaction mixture was maintained at 60° C. for 4 hours with stirring under nitrogen. The resulting prepolymer was cooled to 40° C. and stored in a sealed container under nitrogen.

To 535 parts of the above prepolymer were added 10 parts Cab-O-Sil M5 TM fumed silica commercially available from Cabot Corp., 30 parts toluene, 200 parts Regal TM 300R furnace carbon black (commercially available from Cabot Corp.), 25 parts Mesamoll TM plasticizer (alkylsulphonic ester of phenol, commercially available from Mobay Chemical Corp.), 112 parts of terpene-phenolic resin Piccofyn A-135 available from Hercules Inc. and the amount of the catalysts shown in Table IV. These ingredients were stirred under nitrogen until a uniform mixture was obtained. The resulting mixture was stored in a sealed container.

In a reaction vessel equipped with a stirrer, reflux condenser and a nitrogen atmosphere were combined 1610 parts Desmodur N-75 TM (biuret of hexamethylene diisocyanate commercially available from Mobay Chemical Co.), 427 parts "A-189" gamma-mercaptopropyltrimethoxy silane, and 1.3 parts dimethylpiperazine. The mixture was stirred at 80° C. for two hours and cooled to room temperature. 35 Parts of the resulting silane compound were mixed with the prepolymer/catalyst prepared above.

The rate of strength build up of each sealant was evaluated using the "Flatwise Tensile Test". A 6.4 mm wide ×7.9 mm thick ×101.6 mm long bead of sealant was laid centrally along the long axis of a 76.2 mm ×152.4 mm glass panel, two 6.4 mm spacers were placed on the panel at each end of the bead, a second glass panel of the same dimensions was placed on top of the spacers, and the resulting assembly was inverted and allowed to cure at 24° C. and 50% R.H. The tensile strength of the cure assembly was evaluated using a "Thwing-Albert Intelect-2000" tensile tester operated at a crosshead speed of 508 mm/minute. The following results were obtained using laminated safety glass panels. Unless otherwise indicated, the mode of failure was cohesive, i.e. within the bond.

TABLE IV
Tensile Strength of Adhesives

| | | Catalyst Amount | Tensile Strength (psi) at | | | |
|---|---|---|---|---|---|---|
| Example | Catalyst | (pbw) | 2.7 hr | 5.5 hr | 48 hr | 7 days |
| N | DMDEE* | 1.5 | 10 | 70 | 352 | 676 |
| P | DMDEE | 3.0 | 39 | 103 | 423 | 808 |
| Q | DMDEE | 3.0 | 24 | 92 | 335 | 658 |
| 7 | MEMPE* | 1.5 | 29 | 97 | 578 | 847 |
| 8 | MEMPE | 3.0 | 48 | 130 | 573 | 771 |

*DMDEE is 2,2-dimorpholinyldiethyl ether
*MEMPE is 4-[2-[1-methyl-2-(4-morpholinyl)ethoxy]ethyl]-morpholine

What is claimed is:
1. A composition useful as a catalyst in the curing of a water-curable isocyanate-functional prepolymer com- prising a substantially pure amino ether compound having the structural formula:

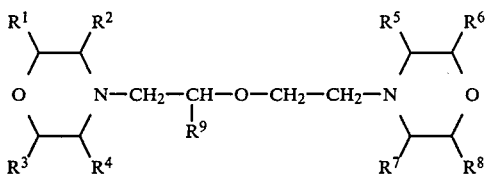

wherein:
  each of $R^1$-$R^8$ are individually hydrogen or lower alkyl; and
  $R^9$ is a methyl group or a phenyl group wherein the phenyl group may have one or more lower alkyl substituents.

2. A composition in accordance with claim 1 wherein $R^9$ is methyl or phenyl.

3. A composition in accordance with claim 1 wherein $R^1$-$R^8$ are individually hydrogen or methyl.

4. A composition in accordance with claim 1 wherein $R^1$-$R^8$ are hydrogen and $R^9$ is methyl.

5. A composition in accordance with claim 1 wherein $R^1$-$R^8$ are hydrogen and $R^9$ is phenyl.

6. A composition comprising an isocyanate-functional prepolymer and an amino ether compound having the structural formula:

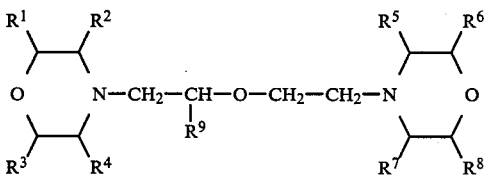

wherein:
  each of $R^1$-$R^8$ are individually hydrogen or lower alkyl; and
  $R^9$ is a methyl group or a phenyl group wherein the phenyl group may have one or more lower alkyl substituents.

7. A composition in accordance with claim 6 wherein the isocyanate-functional prepolymer is a derivative of an aromatic polyisocyanate and a polyether polyol.

8. A composition in accordance with claim 6 wherein the amount of the amino ether compound is from about 0.1% to about 5% by weight of the isocyanate-functional prepolymer.

9. A composition in accordance with claim 6 useful as an adhesive, coating or sealant further comprising a solvent, filler and plasticizer.

10. An article comprised of flexible sheet coated with the composition of claim 6.

11. A composition in accordance with claim 6 herein $R^1$-$R^8$ are hydrogen and $R^9$ is methyl.

12. A composition in accordance with claim 6 wherein $R^1$-$R^8$ are hydrogen and $R^9$ is phenyl.

13. A method of curing an isocyanate-functional prepolymer comprising forming a mixture of water, a water-curable isocyanate-functional prepolymer and a catalytically effective amount of an amino ether compound having the structural formula:

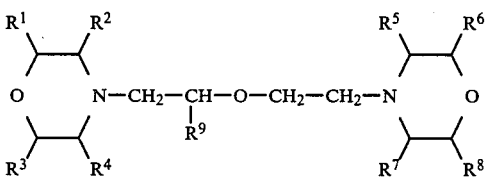

wherein:
  each of $R^1$-$R^8$ are individually hydrogen or lower alkyl; and
  $R^9$ is a methyl group or a phenyl group wherein the phenyl group may have one or more lower alkyl substitutents.

14. A method in accordance with claim 13 wherein the mixture is a coating on a flexible sheet during curing.

15. A method in accordance with claim 14 wherein the sheet material is a porous flexible fabric and the amount of the prepolymer is sufficient to impregnate the porous flexible fabric.

16. A method in accordance with claim 13 wherein $R^1$-$R^8$ are hydrogen and $R^9$ is methyl.

17. A method in accordance with claim 13 wherein $R^1$-$R^8$ are hydrogen and $R^9$ is phenyl.

* * * * *